(12) United States Patent
Jensen et al.

(10) Patent No.: US 8,394,135 B2
(45) Date of Patent: Mar. 12, 2013

(54) INTRODUCER FOR ENDOVASCULAR GRAFTS AND STENTS

(75) Inventors: Kim Moegelvang Jensen, Bjaeverskov (DK); Bent Øhlenschlaeger, Li. Skensved (DK); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 701 days.

(21) Appl. No.: 12/378,094

(22) Filed: Feb. 11, 2009

(65) Prior Publication Data

US 2009/0204198 A1 Aug. 13, 2009

Related U.S. Application Data

(60) Provisional application No. 61/065,332, filed on Feb. 11, 2008.

(51) Int. Cl.
*A61F 2/06* (2006.01)
(52) U.S. Cl. .................................... 623/1.11
(58) Field of Classification Search ............ 623/1.11, 623/1.13, 1.23, 1.12, 2.11; 606/108, 200; 604/531, 532, 530
See application file for complete search history.

(56) References Cited

U.S. PATENT DOCUMENTS

| | | | |
|---|---|---|---|
| 5,219,358 A | | 6/1993 | Bendel et al. |
| 5,762,630 A | * | 6/1998 | Bley et al. ............... 604/164.01 |
| 5,788,713 A | | 8/1998 | Dubach et al. |
| 6,270,496 B1 | | 8/2001 | Bowe |
| 6,602,288 B1 | | 8/2003 | Cosgrove et al. |
| 6,902,555 B2 | * | 6/2005 | Paskar ..................... 604/500 |
| 6,974,471 B2 | | 12/2005 | Van Schie et al. |
| 2004/0015151 A1 | * | 1/2004 | Chambers .................. 604/532 |
| 2004/0073289 A1 | * | 4/2004 | Hartley ..................... 623/1.13 |
| 2005/0049667 A1 | | 3/2005 | Arbefeuille et al. |
| 2006/0074403 A1 | | 4/2006 | Rafiee |
| 2006/0129101 A1 | | 6/2006 | McGuckin, Jr. |

FOREIGN PATENT DOCUMENTS

| | | |
|---|---|---|
| EP | 0646364 | 4/1995 |
| WO | WO 0033909 | 6/2000 |
| WO | WO 2004/045463 | 6/2004 |
| WO | WO 2008/063464 | 5/2008 |

OTHER PUBLICATIONS

Int'l Search Report PCT/US2009/000870, May 8, 2009, EPO.
Written Opinion PCT/US2009/000870, May 8, 2009, EPO.

* cited by examiner

*Primary Examiner* — Gary Jackson
*Assistant Examiner* — Jonathan Hollm
(74) *Attorney, Agent, or Firm* — Brinks Hofer Gilson & Lione

(57) ABSTRACT

An introducer assembly for introducing a stent-graft (70) or other device into a vessel of a patient includes a pre-shaped curved cannula (60) made preferably of a shape memory material. The curved cannula can pull the proximal end (74) of the stent-graft (70) against the inner side wall of the vessel thereby to ensure a good leak free connection at this point. The assembly is particularly useful in deploying stent-grafts into the aortic arch.

18 Claims, 5 Drawing Sheets

INTRODUCER FOR ENDOVASCULAR GRAFTS AND STENTS

CROSS-REFERENCE TO RELATED APPLICATIONS

This application claims priority of provisional application Ser. No. 61/065,332, filed Feb. 11, 2008.

TECHNICAL FIELD

The present invention relates to an introducer for the deployment of implants and prostheses into a body lumen of a patient and in particular for deploying a stent-graft or stent into a patient. The device is particularly suited for the deployment of stent-grafts and stents in the aortic arch.

BACKGROUND ART

Prostheses for the repair of vascular defects, including for example vascular aneurysms, are well known in the art. A common prosthesis for treatment of such a medical condition is a stent-graft.

Prostheses of this type are typically deployed endoluminally through a vein or artery adjacent a surface of a patient. For example, aortic prostheses are commonly fed through the femoral artery. A common method of deployment involves the location of a guide wire along the path to be followed by the introducer assembly, up to the site in the vasculature to be treated. Once the guide wire is in place, a series of catheters is advanced along the guide wire, finally with the introduction of a catheter assembly which carries the stent or stent-graft to be fitted. The catheters have sufficient trackability to follow the guide wire along the curves and turns of the patient's vasculature and some can also curve sufficiently so as to be able to fit a stent-graft, for example, into the aortic arch of a patient.

Even though such a procedure is possible into the aortic arch, it is mired in difficulties as a result of the tight curvature of the latter. One such difficulty arises in connection with the proximal end of the stent-graft, which is liable to be incorrectly fitted such that it incompletely seals around the inner wall of the aorta as a result of the curvature imparted to the stent-graft. This can lead to leakage of blood around the outside of the stent-graft and thus of a less than effective treatment. Furthermore, as a result of the non-optimal placement of the stent-graft using known procedures, there is a limit to the length of neck of healthy vascular wall which is needed to provide a seal around the proximal end of the stent-graft. This limits the application of such stent-grafts, in particular for the treatment of aneurysms close to a branch vessel. In addition, in some instances at least, a part of the proximal end of the stent-graft can remain loosely located in the vessel, leading to premature fatigue failure and thrombus effects.

Attempts have been made to resolve these difficulties. For instance, in the applicant's U.S. Pat. No. 6,974,471, mechanisms are described for imparting a curvature to the stent-graft at the moment of its deployment.

A number of other types of device seek to provide medical devices which can be curved in situ but these are not related to the deployment of stents or stent-grafts or able to be used in any such application. Such other devices are disclosed, for example, in U.S. Pat. No. 6,602,288, US-2006/0,129,101, U.S. Pat. No. 5,788,713, U.S. Pat. No. 6,270,496, U.S. Pat. No. 5,219,358, US-2006/0,074,403 and WO-00/33,909.

DISCLOSURE OF THE INVENTION

The present invention seeks to provide an improved introducer system for introducing a medical device into a patient.

According to an aspect of the present invention, there is provided an introducer assembly for introducing a stent-graft or other device into a patient, including a catheter provided with a flexible device holding portion onto which a device to be introduced into a patient can be placed, the device holding portion being formed in a curve so as to impart a curvature to a device placed thereon and being able to be trained between substantially straight and curved configurations.

In the preferred embodiment, the device holding portion is able to be trained between substantially straight and curved configurations by the introducer assembly. It may, likewise, be trainable by another mechanism, including by being formed of a shape memory material and trained to a curved memory shape.

The curvature of the device holding portion can assist in the correct orientation and thus deployment of a stent-graft held thereon, particularly for deployment within the aortic arch or other vascular location or configuration having a tight radius of curvature. In practice, the preferred embodiment provides a cannula which imparts an inwards-acting force on the proximal end of the medical device, so as to force this against the vessel wall at the interior of the curve.

In one embodiment, the introducer assembly includes an outer sheath within which the catheter can be provided, the catheter being slidable within the outer sheath between a retracted position and an extended deployment position, the outer sheath acting to straighten the holding portion of the catheter when in the retracted position.

In another embodiment, the introducer assembly includes a guide wire having a relatively stiff portion or being substantially relatively stiff along its length, the device holding portion being provided with a bore therethrough for receiving the guide wire, wherein the guide wire is operable to straighten the device holding portion relative to the guide wire. In an embodiment, the guide wire may be provided with a flexible distal tip portion, wherein the device holding portion is able to bend when disposed over the flexible distal tip portion of the guide wire.

The above embodiment can be useful in assemblies which do not rely upon a traditional sheath for protecting and introducing a stent-graft or other device, such as those which use instead a wrapping, film or other covering. In this case, the guide wire acts to train the device holding portion of the catheter. In the preferred embodiments, the introducer assembly includes both a sheath and such a guide wire. In such a case, the sheath and the guide wire can be used together to change the curvature of the device holding portion in a variety of ways during the deployment procedure.

Advantageously, the outer sheath and/or guide wire is flexible, so as to be able to follow a tortuous path until the treatment site, the device holding portion of the catheter advantageously having a lower deflection force than that of the sheath and/or guide wire. Most preferably, the deflection force for deflecting the device holding portion of the catheter is sufficiently lower than the force required to deflect the outer sheath and/or guide wire, so as to have minimal variation to the flexibility of the introducer in operation.

In an embodiment, the device holding portion of the catheter is a cannula.

Advantageously, the device holding portion is formed from a shape memory material. In the preferred embodiment, the device holding portion is made of a suitable Nickel Titanium alloy such as Nitinol, formed to have shape memory characteristics. Other possible materials include super elastic shape memory alloys such as Cu—Al—Ni, Cu—Al—Zi and Cu—Zi, preferably coated. The device holding portion may also be made of a shape memory polymer of the types known in the art.

The use of a shape memory material for the device holding portion, which has a transition temperature around body temperature, imparts to this portion conformability during initial phases of deployment, useful in reducing the bending forces required in the process of insertion of the introducer into a patient and a greater bending force upon heating of the holding portion to body temperature. Thus, this can contribute to minimizing the effects on the radial flexibility of the outer sheath and thus to minimizing any effects on the trackability of the introducer.

In a preferred embodiment, the device holding portion relies upon the super elastic properties of such as shape memory material, which is used substantially entirely in its austenitic phase, that is by choosing an alloy with a temperature substantially below body temperature so as to be used in its austenitic phase throughout the procedure. It has been found, for instance with Nickel Titanium alloys such as Nitinol, that the device holding portion can exhibit a much greater force of curvature than, for example, a similar device made of stainless steel.

In other embodiments, the device may be made of a sprung material such as spring steel. It has been found that a combination of a spring steel device holding portion and a wire guide for control of the curvature thereof is particularly effective.

The device holding portion may have a natural curvature conforming to that of the aortic arch and preferably greater than the curvature of the aortic arch, although this is not necessary. The term natural curvature is intended to refer to curvature in the absence of external forces tending to change the curvature of the device holding portion.

It is envisaged that the holding portion may be curved to the extent of having substantially a U-shape when unbiased. Preferably, the holding portion curves such that the distal and proximal ends thereof are closer to one another than the radius of curvature of the holding portion, that is that the ends bend into one another. Such a curvature ensures that the holding portion will have a curvature greater than the curvature of the aortic arch.

In some embodiments, the holding portion can have a smaller angle of curvature. For example, in some embodiments it has been found that a curvature of around 90° can perform well, particularly in embodiments where the device holding portion is provided with a tight curved end adjacent its distal tip, that is adjacent the dilator tip. Such an embodiment allows the device holding portion to be used as a tool for pushing the stent-graft or other device against the vessel walls, by moving and rotating the introducer tip around the inner circumference of the device being deployed.

Advantageously, the holding portion has a radius of curvature in the region of 3.5 centimeters or less. Embodiments have been tested with radii of curvature of 2 to 3.5 cm, of 1 cm and even as low as 0.5 cm. A smaller radius of curvature provides a greater device urging force and can be used even in very tight vascular bends, even for treating children.

Having a device holding portion with such a curvature ensures that its proximal end and thus the proximal end of the device are always urged against the inner wall of the artery, in practice ensuring a good connection between the device and the aorta wall.

The preferred embodiments provide several other advantages over the prior art. A precise and effective coupling of the proximal end of a stent-graft to the vessel wall enables not only a better and more reliable seal but also deployment in patients having a much shorter neck length for coupling and in lumens having a much tighter curvature than possible with prior art systems. Furthermore, in embodiments where the device holding portion is of an entirely elastic nature, it can cause the distal end of the introducer to curve slightly. Such a slight curvature can provide self-orientation of the introducer in a curved part of a patient's vasculature, which can be particularly useful in the deployment of asymmetric stent-grafts, fenestrated stent-grafts, branched stent-grafts and so on. The slight curvature can provide an indication of orientation of the tip of the introducer, and thus of the device carried thereon, within the patient's vessels.

According to another aspect of the present invention, there is provided a catheter for an introducer assembly for introducing a stent-graft or other device into a patient, the catheter including a flexible device holding portion onto which a device to be introduced into a patient can be placed, the device holding portion being formed in a curve so as to impart a curvature to a device placed thereon and being able to be trained between substantially straight and curved configurations.

According to another aspect of the present invention, there is provided a method of deploying a device in a patient, including the steps of: providing an introducer assembly for introducing a stent-graft or other device into a patient, the assembly including a catheter provided with a device holding portion onto which a device to be introduced into a patient is placed, the device holding portion being formed in a curve, the assembly including an outer sheath operable to house the catheter and device and/or a guide wire locatable in a lumen of the device holding portion; the method including the steps of inserting a proximal end of the introducer endoluminally into a patient to the point of a vascular arch, withdrawing the catheter from the outer sheath and/or withdrawing the guide wire form the device holding portion, providing for the device holding portion to curve around the vascular curve, urging an inner edge of the device against a vascular wall, and releasing the device from the introducer.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

For the purposes of this disclosure, when used in connection with description of a stent-graft or other implantable device, the term "proximal" refers to a part or position closest to the heart, that is upstream in the direction of blood flow, while the term "distal" refers to a part or position furthest from the heart. On the other hand, when used in connection with an introducer assembly the term "proximal" refers to a position or part closest to the surgeon and typically kept outside the patient, while the term "distal" refers to a position or part furthest from the surgeon and in practice furthest into a patient during a deployment procedure.

Figure 1:
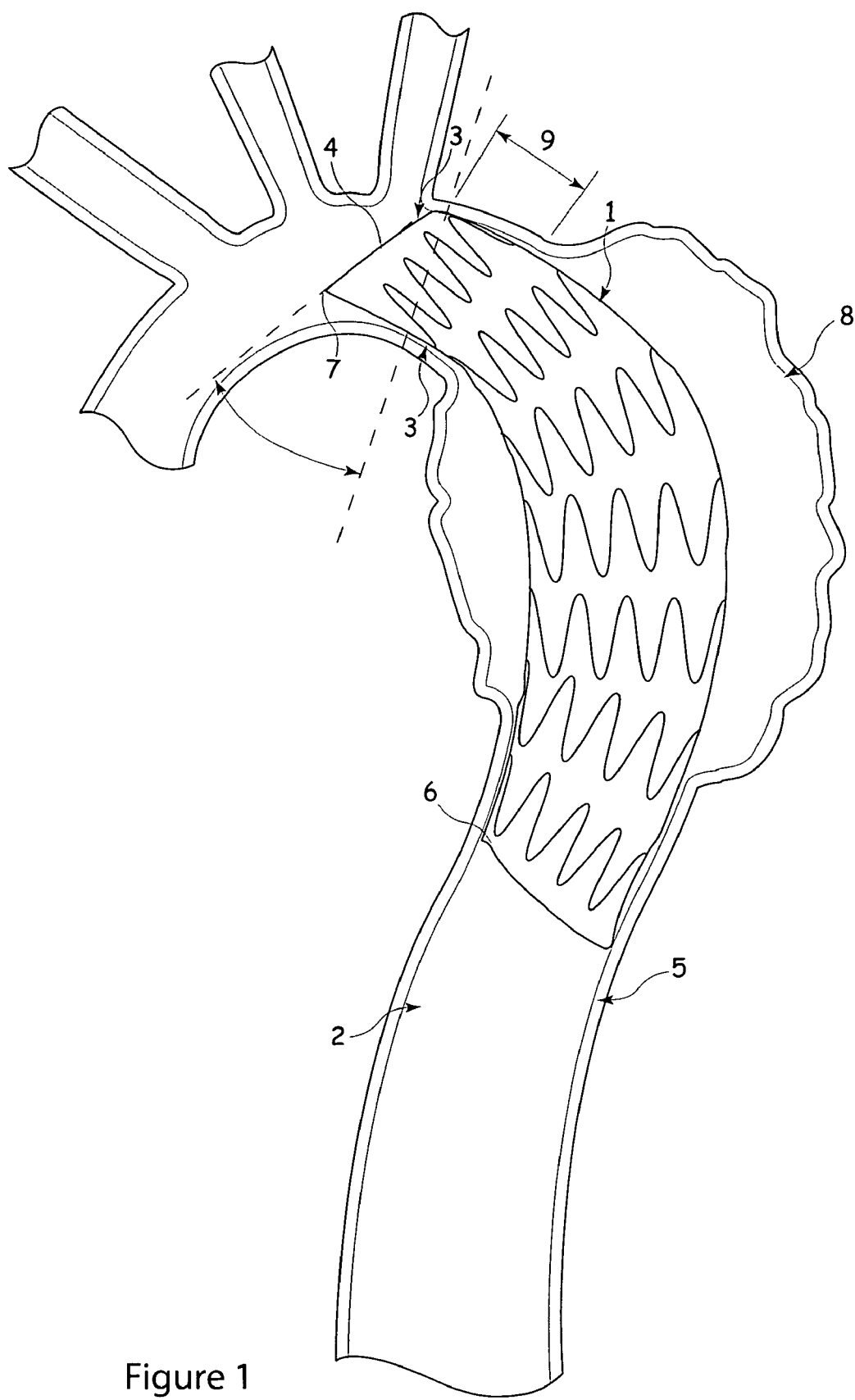
FIG. 1 shows an example of stent-graft deployed in the aortic arch by a prior art introducer system.

Referring to FIG. 1, there is shown an example of deployment of a stent-graft 1 within the aorta 2 of a patient for the treatment of, for example, an aneurysm 8. In this particular example, the stent-graft extends part-way into the aortic arch 3 at its proximal end 4, down to the thoracic aorta 5 at its distal end 6. The curvature of the aortic arch 3, coupled with use of a conventional introducer system which follows the arch 3 by being bent thereby, can cause the proximal end 4 of the stent-graft 1 to be located incorrectly, that is not to have its opening, that is the front edge of the stent graft, perpendicular with the vessel at that position. When this occurs, the proximal part of the stent graft 1 and in particular the proximal-most stent does not align properly with the vessel wall. As a result, the inner side 7 of the stent-graft 1 stands proud of the vessel wall, being spaced therefrom. The angle A at which the proximal end 4 lies deviates from the perpendicular line B. The resultant gap between the inner side 7 and the aortic wall provides a path for leakage of blood, which can lead to failure of the stent-graft in achieving its intended function. In practice, such imprecise deployment results in it being necessary to have a relatively long neck 9 to achieve a reliable seal between the stent-graft 1 and the vessel wall. Thus, medical conditions which do not have a sufficient length of neck 9, that is of healthy vessel wall, cannot at present be treated.

In addition to these problems, the end 7 of the stent-graft tends to flap in the force of blood flow, leading to fatigue wear and to thrombus formation.

Figure 2:
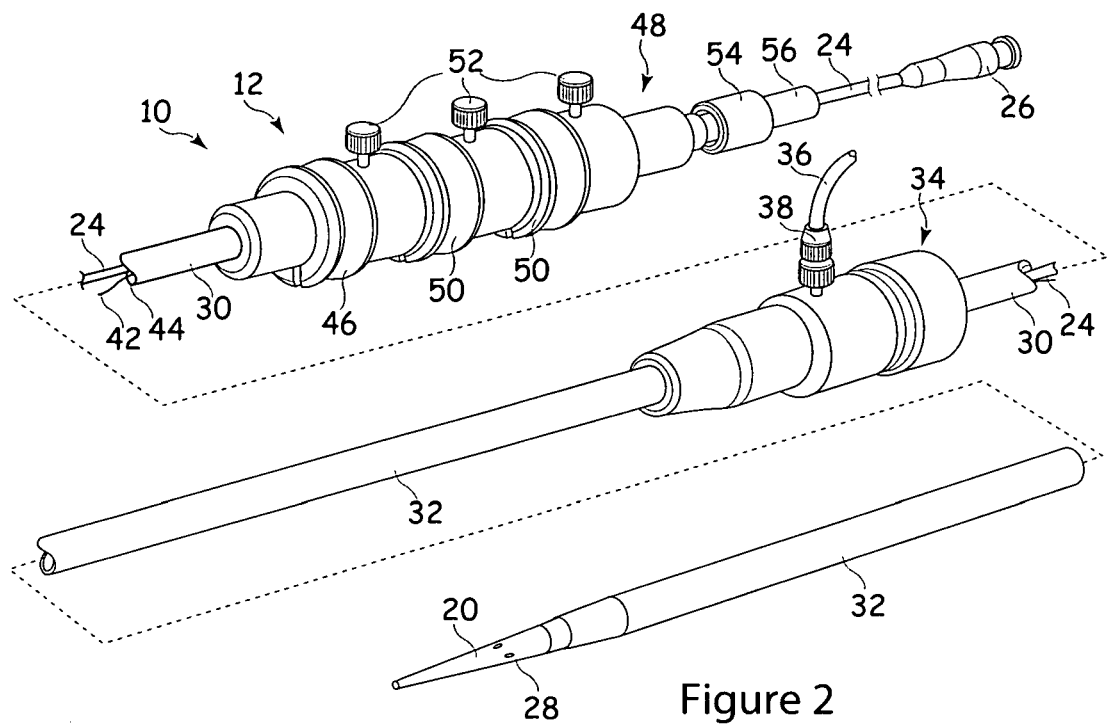
FIGS. 2 and 3 are perspective views of an example of introducer system which can be used with the present invention.
Figure 3:
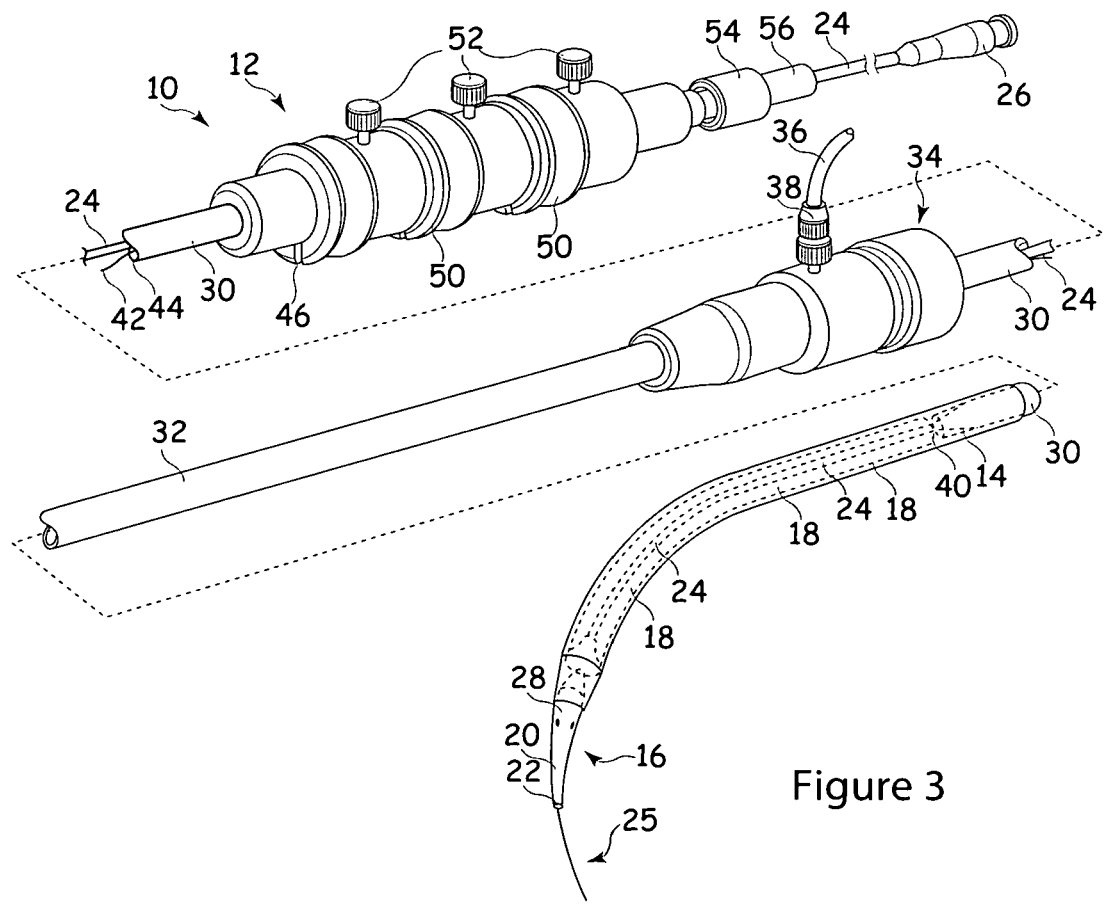

Referring now to FIGS. 2 and 3, there is shown an example of introducer of the type used in the deployment of stent-grafts of the form shown in FIG. 1. The introducer 10 includes an external manipulation section 12, a distal attachment region 14 and a proximal attachment region 16. The distal attachment region 14 and the proximal attachment region 16 secure the distal and proximal ends of the implant 18, respectively. During the medical procedure to deploy the implant 18, the distal and proximal attachment regions 14 and 16 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a dilator tip 20, which is typically provided with a bore 22 therein for receiving a guide wire 25 of conventional type. The longitudinal bore 22 also provides a channel for the introduction of medical reagents. For example, it may be desirable to supply a contrast agent to allow angiography to be performed during placement and deployment phases of the medical procedure.

A guide wire catheter 24, conventionally made from a flexible thin walled metal tube, is fastened to the dilator tip 20. The guide wire catheter 24 is flexible so that the introducer 10 can be advanced along a relatively tortuous vessel, such as a femoral artery, and so that the distal attachment region 14 can be longitudinally and rotationally manipulated. The guide wire catheter 24 extends through the introducer 10 to the manipulation section 12, terminating at a connection device 26, in conventional manner.

The connection device 26 is designed to accept a syringe to facilitate the introduction of reagents into the inner catheter 24. The guide wire catheter 24 is in fluid communication with apertures 28 in the flexible dilator tip 20. Therefore, reagents introduced into connection device 26 will flow to and emanate from the apertures 28.

A pusher sheath or rod 30 (hereinafter referred to as a pusher member), typically made from a plastics material, is mounted coaxial with and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by this device 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher rod 30. The side tube 38 facilitates the introduction of medical fluids between the pusher rod 30 and the sheath 32. Saline solution is typically used.

During assembly of the introducer 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher rod 30 and retains a distal end 40 of the prosthesis 18 during the procedure. The distal end of the prosthesis 18 is provided with a loop (not shown) through which a distal trigger wire 42 extends. The distal wire also extends through an aperture (not shown in FIGS. 1 and 2) in the distal attachment section 40 into an annular region 44 between the inner catheter 24 and the pusher rod 30. The distal trigger wire 42 extends through the annular space 44 to the manipulation region 12 and exits the annular space 44 at a distal wire release mechanism 46.

A proximal portion of the external manipulation section 12 includes at least one release wire actuation section 50 mounted on a body 48, in turn mounted onto the pusher member 30. The guide wire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism 46 must be moved before the distal wire release mechanism or mechanisms 50 can be moved. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire catheter 24. When the vise jaws are engaged, the guide wire catheter 24 can only move with the body 48 and hence it can only move with the pusher member 30. With the screw cap 56 tightened, the entire assembly can be moved together as one piece.

Once the introducer assembly 12 is in the desired deployment position, the sheath 32 is withdrawn to just proximal of the distal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end self-expanding stent however, is still retained at the dilator tip 16 by means of the release wires. Also, the distal end of the stent or stent-graft 18 will still retained within the sheath 32.

Next, the pin vise 54 is released to allow small movements of the guide wire catheter 24 with respect to the pusher rod 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the prosthesis.

When the proximal end of the stent or stent-graft 18 is in place, the proximal trigger wire is withdrawn by distal movement of the proximal wire release mechanism. The proximal wire release mechanism 50 and the proximal trigger wire can be completely removed by passing the proximal wire release mechanism 50 over the pin vise 54, the screw cap 56 and the connection unit 26.

Next, the screw cap 56 of the pin vise 54 is loosened, after which the inner catheter 24 can be pushed in a proximal direction to move the dilator tip 20 in a proximal direction. When the dilator tip 20 no longer surrounds the end of the stent or stent-graft 18, it expands to engage the lumen walls of the patient. From this stage on, the proximal end of the stent or stent-graft 18 cannot be moved again.

Once the proximal end of the stent or stent-graft 18 is anchored, the sheath 32 is withdrawn distally of the distal attachment section 14, which withdrawal allows the distal end of the stent or stent-graft 18 to expand. At this point, the distal end of the stent or stent-graft 18 may still be repositioned as needed.

As will be apparent in particular from FIG. 3, the distal end of the introducer is flexible, so as to be able to follow a tortuous path of a patient's vasculature, as well as in some applications to locate a stent-graft in a curved portion of a lumen such as the aortic arch. The distal end curves, however, by being pulled into this configuration as a result of curving of the guide wire, which is itself urged into a curved shape by the curvature of the lumen. As a result of this, the distal end of the introducer tends to follow the outside of any curve. When deployment occurs in such a situation, as it does in the aortic arch for example, the stent-graft can become improperly located, as in the example of FIG. 1.

The applicant's earlier U.S. Pat. No. 6,974,471 describes a variety of mechanisms for imparting a curvature to the stent-graft at the moment of its deployment, primarily by mechanisms which act to pull on the proximal (upstream) end of the stent-graft.

The present invention seeks to address the problem with prior art introducer systems and in a way which does not alter the assembly of the stent-graft or add additional components to the introducer device. Moreover, the preferred embodiments provide a system which can enhance the fitting of the stent-graft into a lumen, particularly at the aortic arch and other highly curved regions of a patient's vasculature.

Figure 4:
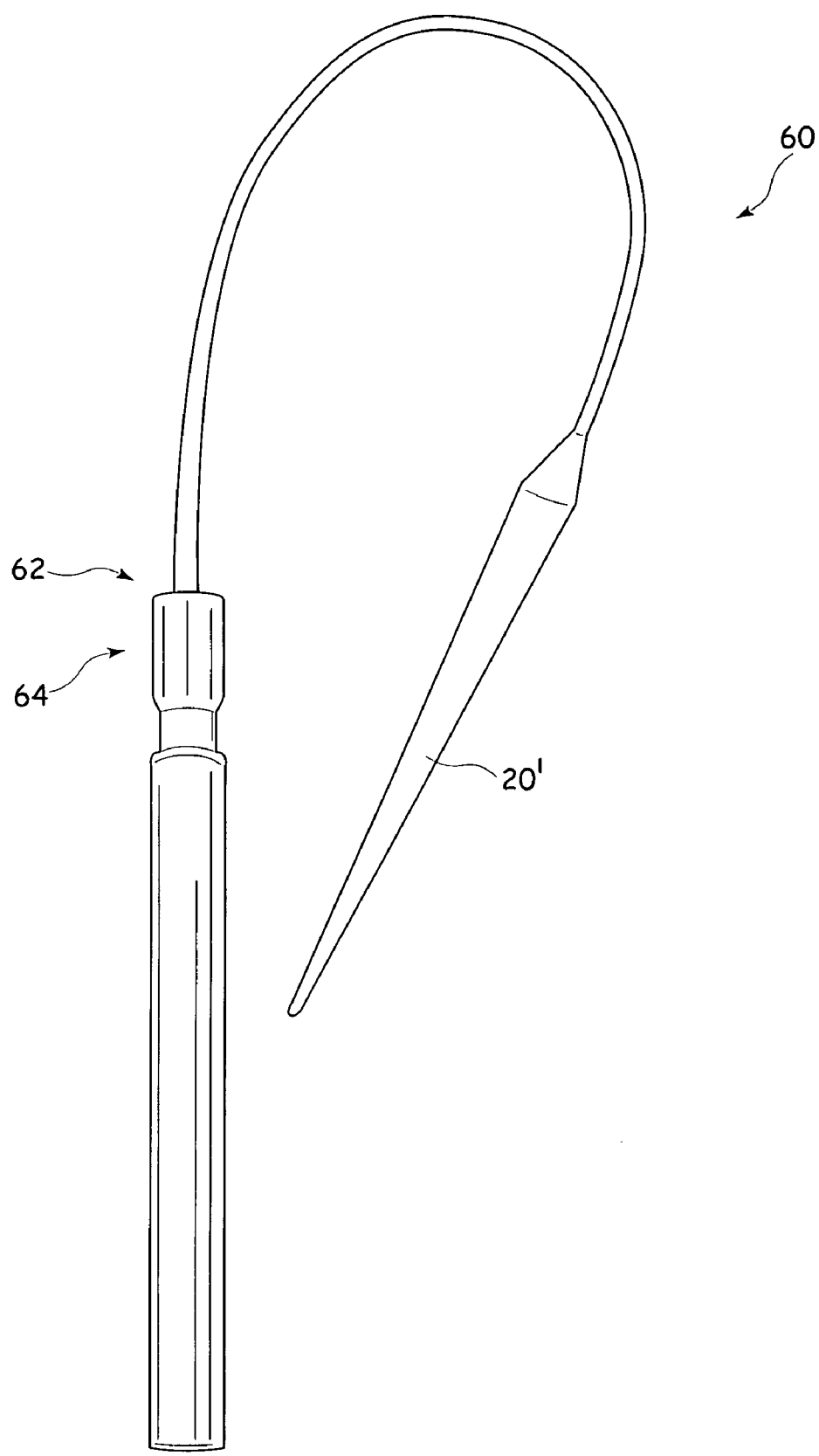
FIG. 4 is a side elevational view of a preferred embodiment of distal end of an introducer according to the present invention.

Referring now to FIG. 4, there is shown an embodiment of inner catheter or cannula 60. In practice this would replace the catheter 24 of the device of FIGS. 2 and 3. However, the cannula 60 could be used in other types of introducer, including introducer systems which do not rely upon an outer sheath of the type shown in FIGS. 2 and 3 but on another stent-graft covering such as a wrapping, film or the like.

The cannula 60 is formed in a curved shape, in the preferred embodiment being such that the tip 20' is rotated by around 180°, most preferably even more than this such that its ends point into one another as shown in the example of FIG. 4.

In some embodiments, the cannula 60 may have a lower angle of curvature. For example, in some embodiments it has been found that a curvature of around 90° can perform well, particularly in cases where the cannula 60 is provided with a tight curved end adjacent its distal tip 20', that is adjacent the dilator tip. Such an embodiment allows the cannula 60 to be used as a tool for pushing the stent-graft or other device against the vessel walls, by moving and rotating the introducer tip 20' around the inner circumference of the device 70 being deployed.

Advantageously, the cannula 60 has a radius of curvature in the region of 3.5 centimeters or less. Embodiments have been tested with radii of curvature of 2 to 3.5 cm, of 1 cm and even as low as 0.5 cm. A smaller radius of curvature provides a greater device urging force and can be used even in very tight vascular bends, for example of the type which might be found in children.

The cannula 60 is made from a material which is flexible such that during the deployment procedure it can be straightened. In one embodiment, the cannula 60 is made of a shape memory material, most preferably an alloy of Titanium and Nickel, such as Nitinol. Other alloys having shape memory properties could also be used, such as alloys of Cu—Al—Ni, Cu—Al—Zi and Cu—Zi, preferably coated for optimum biocompatibility. It may also be made of a shape memory polymer of the types known in the art, such as polyamide.

The advantage of shape memory materials is that they can be made to be super elastic until they reach their transition temperature, in this application around body temperature, thus exhibiting little adverse effect on the deployment operation until the point at which it is desired they take their memory shape.

In other embodiments, the cannula 60 is formed of a material which exhibits super-elastic properties for all of the conditions in which it is used. The cannula 60 would thus always exhibit a force of curvature when trained into any other angle or straightened. Such cannulae 60 can be formed of any suitable elastic material, including shape memory materials formed to as to have very low transition temperatures, that is to be in their austenitic phases even prior to implantation of the introducer into a patient. The examples of materials given above are suitable although it is preferred to use a Nickel Titanium alloy such as Nitinol as this provides a substantially greater force of curvature than, for example, stainless steel. Other examples include spring steel.

It is envisaged also that in some embodiments the cannula could be formed of a shape memory material which is designed to transition to its memory shape during the course of deployment, thereby not to display any significant curvature during the initial phase of deployment and only when the introducer is positioned in the deployment location.

The cannula 60 is preferably provided with features of known cannulae, such as apertures and receptacles for holding and handling trigger wires, and a central bore for the passage of a guide wire 25 therethrough. At a proximal end 62 of the cannula 60 there is provided a pusher 64, of known type, for abutment against the distal end of a stent-graft until deployment. A suture typically ties the stent-graft to the pusher until its release.

Thus, a stent-graft will be fitted to the cannula 60 with its proximal end tied closed adjacent the dilator tip 20' and its distal end held against and tied to the pusher 64. The elements shown in FIG. 4 would be covered by an outer sheath such as the sheath 32 shown in FIGS. 2 and 3, in known manner. When in the sheath 32, the cannula 60 is held substantially straight. It is preferred that the cannula 60 is of dimensions and a thickness such that the bending force caused by the curvature of the cannula 60 is insufficient to cause more than minimal curvature of the sheath 32 and most preferably to cause minimal alteration to the radial flexibility of the sheath 32 and thus of the distal end of the introducer system. By use of shape memory materials for the cannula 60, this can be made to retain its plastic properties while in the sheath 32 and until it has been heated sufficiently by the patient's body heat to undergo its phase transition to return to its memorised shape. In this event, the cannula 60 will exhibit substantially no non-uniform effect on the flexibility or curvature of the sheath 32 until deployment, which might otherwise be caused by its memorised curvature.

In other embodiments, a stiff wire guide is used with the assembly, which has the added benefit of acting as the element which trains the cannula 60 into a substantially straight configuration, until the wire guide is withdrawn from the cannula 60. In some cases, the wire guide could be provided with a soft distal portion, whereupon the wire guide can be kept in place over the cannula 60 while still allowing the cannula to return towards its natural curved shape once the wire guide is withdrawn sufficiently to place its softer portion within the cannula 60.

In some instances a combination of a sheath 32 and a wire guide 25 may be used. This can provide additional adjustability to the introducer, for example by withdrawing one of the sheath and guide wire before the other.

Although some embodiments make use of a straightened cannula 60, by shape memory effect or suitable cannula or wire guide, it is envisaged that in some applications it is preferred to impart some curvature to the distal end of the introducer. Such curvature can provide a self-orienting effect to the introducer, particularly useful for the deployment of asymmetric stent-grafts, fenestrated stent-grafts and branched stent-grafts.

Figure 5:
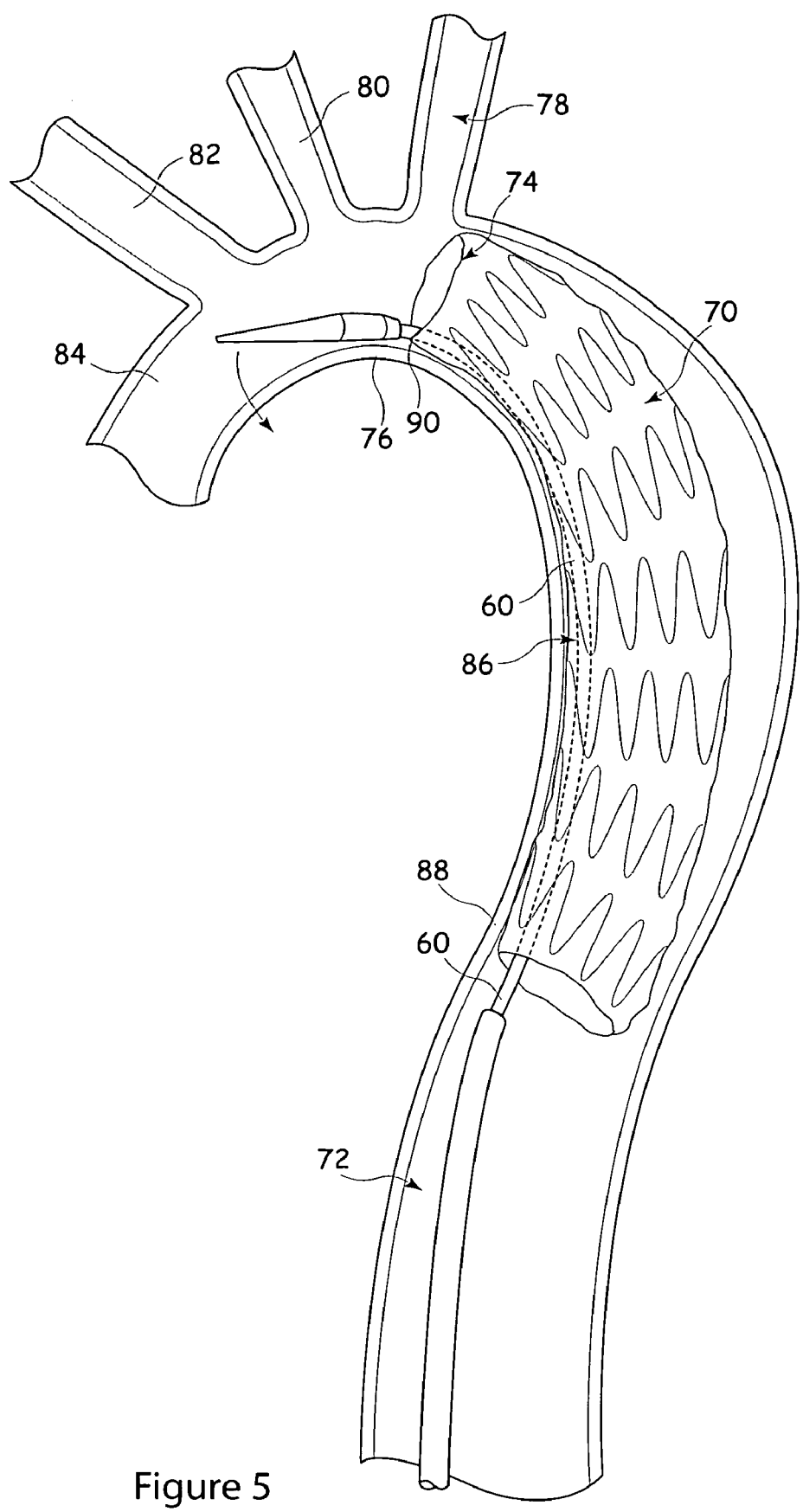
FIG. 5 is a schematic view of a stent-graft being deployed in the aortic arch by an introducer system having the distal end of FIG. 4.

Referring now to FIG. 5, there is shown the embodiment of introducer including the inner catheter or cannula 60 of FIG. 4 in the process of deploying a stent-graft 70 in an aorta 72 of a patient. The proximal end 74 of the stent-graft 70 is being positioned in the aortic arch 76, just short of the left subclavian artery 78, in this example. The introducer is equally suited to the deployment of a suitable stent-graft beyond the left subclavian artery 78, as well as beyond the left common carotid artery 80 and the brachiocephalic artery 82 and into the ascending aorta 84. Fenestrated or branched stent-grafts for such applications are known in the art.

As can be seen in FIG. 5, the stent-graft 70 is in the process of expanding in the aorta 72. During this process, the cannula 60 curves by its memorised or natural curvature into the aortic arch 76, pulling with it the inner side 86 of the stent-graft 70, such that this follows the curve of the inner side 88 of the aortic wall. In particular, the cannula 60 pulls the inner side 90 of the proximal end 74 of the stent-graft 70 against the aortic wall, ensuring a good coupling of the stent-graft 70 to the aortic wall. The cannula thus has the effect of compressing the inner side of the stent-graft against the vessel wall, thereby to assist in compressing the stent-graft in its longitudinal extent, a factor necessary in providing a good fit on the inside of the curve of the vessel, which is shorter than its wall length on the outside of the curve. This feature is particularly useful in the deployment of stent-grafts which are loaded onto the cannula 60 in a "stretched out" condition, the latter being more suitable to the outer side of the curve rather than the shorter inner side.

In practice, the stent-graft is provided, as is known in the art, with a plurality of barbs (not shown) to fix the stent-graft to the vessel wall. By pulling the proximal end 74 of the stent-graft 70 against the inner wall of curvature, the cannula 60 ensures that the barbs on the inner side of the curve of the stent-graft 70 can embed properly into the vessel wall.

In the case of a cannula 60 made of shape memory material, before the deployment procedure and also during the first stage of deployment, that is of feeding of the introducer to the target site, the cannula 60 is kept below its transition temperature such that it can be trained to a substantially straight condition and then made to follow the curving of the introducer during the first stage of the procedure. During this stage, the cannula 60 will impart substantially no unilateral bending force to the sheath 32 and thus to the introducer, enabling this to behave substantially identically to a prior art introducer.

In the course of the deployment procedure and in particular during withdrawal of the outer sheath 32, the cannula 60 will be heated, as a result of the patient's body heat, to above its transition temperature and thus to seek to return to its memory shape, that is to the curved shape shown in FIG. 4. This will thus occur as the stent-graft 70 is being trained into position, in this example in the aortic arch, thus having the effect of pulling the stent-graft 70 into the position shown in FIG. 5.

In the case of a cannula 60 which retains its sprung characteristics, that is not of a type which transitions to a memorised shape or which does so at a relatively low temperature and before commencement of the deployment procedure, the cannula 60 will be trained or biased to a substantially straight configuration by the sheath 32 and/or the guide wire 25 and will follow the path of these during the insertion process. As a result of the retained force of curvature of the cannula 60, there may be a certain curvature of the distal end of the introducer, which can be advantageous in cases where a particular orientation of the prosthesis or other implant is desired, such as in the case of an asymmetrical device. Thus, the curvature of the cannula 60 can provide a degree of self-orientation to the introducer.

In this embodiment, as the sheath 32 and/or the guide wire 25 is retracted, the cannula 60 is released from its constrained condition and can flex fully towards its natural curved configuration, in so doing pulling with it the stent-graft or other device towards the inner wall of the vessel to as to plant the device properly against the wall.

The tight curvature of the preferred embodiment of cannula 60 shown in FIG. 4 ensures that the proximal end 74 of the stent-graft 70 is pulled against the inner side of the vessel wall irrespective of the dimensions or curvature of the aortic arch 76 or the specific positioning of the stent-graft 70 to treat the particular medical condition.

Figure 6:
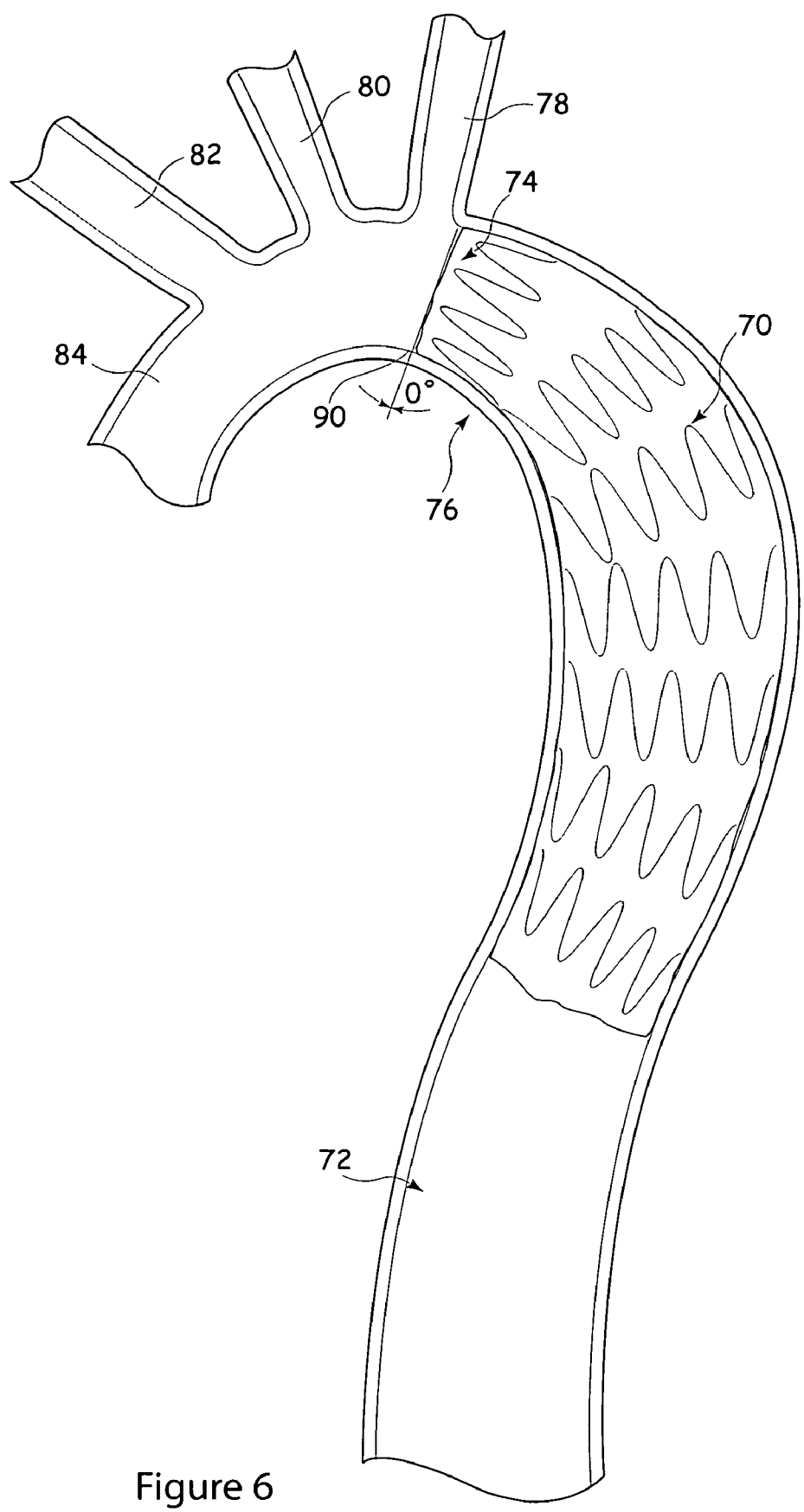
FIG. 6 shows the stent-graft of FIG. 6 when fully deployed.

The end result of the procedure is shown in FIG. 6. As can be seen, the stent-graft 70 is properly deployed in the vessel, with the proximal face 74 lying correctly aligned with the perpendicular to the vessel, such that the proximal-most stent is aligned substantially parallel to the vessel wall and the stent-graft 70 is sealed to the vessel wall all around its circumference, including at the radially internal side 90, leaving no gap for blood leakage.

The precise and reliable placement of the proximal end 74 of the stent-graft 70 can be effected in a much shorter neck length of vessel wall compared to the less reliable prior art systems. Thus, it is possible with this introducer system to fit stent-grafts and other prostheses and implants to patients who cannot be treated by current procedures, for example who suffer from aneurysms too close to a branch vessel or which otherwise have a very short neck length of healthy vessel wall. Furthermore, the introducer system taught herein allows the placement of stent-grafts and other devices in vessels having a much tighter curvature than can be achieved with existing systems.

FIG. 4 shows a cannula 60 which is curved throughout its length along the device carrying portion thereof. That is, the proximal and distal ends of the cannula 60 have slight curvatures, whereas its central portion has a much tighter curve. Moreover, the tip 20' points in towards the sheath 32. This shape, although preferred, is not critical to the performance of the cannula 60, as will already be apparent from the disclosure above. Other shapes are envisaged, including, for example, a cannula having a curved intermediate portion located between straight distal and end portions. Similarly, as explained above, the cannula could be formed to have a bend or tight curve, such as proximate the dilator tip 20'.

The described embodiments also make reference to the deployment of a stent-graft in the aortic arch. The introducer could be used to deploy a wide variety of medical devices including, for example, stents, as well as in other parts of a patient.

What is claimed is:

1. An introducer assembly for introducing a stent-graft or other device into a patient at the patient's aortic arch, including a catheter provided with a flexible device holding portion onto which a device to be introduced into a patient can be placed, the device holding portion being a cannula and being formed in a curve so as to impart a curvature to a device placed thereon and being able to be trained between substantially straight and curved configurations; wherein, in the curved configuration, the device holding portion has a radius of curvature of no more than 3.5 centimeters so as to cause said flexible device holding portion to be trained to the inner curvature of the wall of a curved vessel of a patient.

2. An assembly according to claim 1, wherein the device holding portion is operable to be trained between said substantially straight and curved configurations by the introducer assembly.

3. An assembly according to claim 2, including an outer sheath within which the catheter can be provided, the catheter being slidable within the outer sheath between a retracted position and an extended deployment position.

4. An assembly according to claim 2, including a guide wire including a relatively stiff portion, the device holding portion being provided with a bore therethrough for receiving the guide wire, wherein the guide wire is operable to straighten the device holding portion relative to the guide wire.

5. An assembly according to claim 4, wherein the guide wire is relatively stiff for substantially the entirety of its length.

6. An assembly according to claim 4, wherein the guide wire is provided with a flexible distal tip portion, wherein the device holding portion is able to bend when disposed over the flexible distal tip portion of the guide wire.

7. An assembly according to claim 2, wherein the assembly includes an outer sheath and a guide wire, wherein at least one of the outer sheath and the guide wire acts to straighten the holding portion of the catheter when the latter is held on or in the catheter or guide wire.

8. An assembly according to 7, wherein the outer sheath and the guide wire are flexible, the device holding portion of the catheter having a lower deflection force than that of at least one of the outer sheath and the guide wire.

9. An assembly according to claim 8, wherein the deflection force for deflecting the device holding portion of the catheter is sufficiently lower than the force required to deflect said at least one of the outer sheath and the guide wire to minimise variation to the flexibility of the introducer in operation.

10. An assembly according to claim 1, wherein the device holding portion is formed from a shape memory material.

11. An assembly according to claim 10, wherein the device holding portion is made of a Nickel Titanium alloy.

12. An assembly according to claim 10, wherein the device holding portion is made of a shape memory polymer.

13. An assembly according to claim 10, wherein the material of the device holding portion has a transition temperature around body temperature.

14. An assembly according to claim 10, wherein the material of the device holding portion has a transition temperature below body temperature.

15. An assembly according to claim 1, wherein the device holding portion has a curvature such as to give is substantially a U-shape when unbiased.

16. An assembly according to claim 1, wherein the device holding portion has a curvature of greater than 180°.

17. A catheter for an introducer assembly for introducing a stent-graft or other device into a patient at the patient's aortic arch, the catheter including a flexible device holding portion onto which a device to be introduced into a patient can be placed, the device holding portion being a cannula and being formed in a curve so as to impart a curvature to a device placed thereon and being able to be trained between substantially straight and curved configurations; wherein, in the curved configuration, the device holding portion has a radius of curvature of no more than 3.5 centimeters so as to cause said flexible device holding portion to be trained to the inner curvature of the wall of a curved vessel of a patient.

18. A method of deploying a device in a patient, including the steps of: providing an introducer assembly for introducing a stent-graft or other device into a patient, the assembly including a catheter provided with a device holding portion onto which a device to be introduced into a patient is placed, the device holding portion being a cannula and being formed in a curve, the assembly including an outer sheath operable to house the catheter and device and/or a guide wire locatable in a lumen of the device holding portion; the method including the steps of inserting a proximal end of the introducer endoluminally into a patient to the point of a vascular arch, withdrawing the catheter from the outer sheath and/or withdrawing the guide wire from the device holding portion, providing for the device holding portion to curve around the vascular curve, urging an inner edge of the cannula toward an inner curvature of a vascular wall, and releasing the device from the introducer.

* * * * *